(12) United States Patent
Pacetti

(10) Patent No.: US 6,712,844 B2
(45) Date of Patent: Mar. 30, 2004

(54) MRI COMPATIBLE STENT

(75) Inventor: Stephen Dirk Pacetti, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 333 days.

(21) Appl. No.: 09/876,756

(22) Filed: Jun. 6, 2001

(65) Prior Publication Data

US 2002/0188345 A1 Dec. 12, 2002

(51) Int. Cl.⁷ ................................................ A61F 2/06
(52) U.S. Cl. .................................. 623/1.15; 623/1.16
(58) Field of Search .......................... 623/1.1, 1.15, 623/1.16, 1.17, 1.18–1.22

(56) References Cited

U.S. PATENT DOCUMENTS

| | | | |
|---|---|---|---|
| 4,661,530 A | 4/1987 | Gogolewski et al. | |
| 4,830,003 A | 5/1989 | Wolff et al. | |
| 5,320,100 A | 6/1994 | Herweck et al. | |
| 5,630,829 A | * 5/1997 | Lauterjung | 606/198 |
| 5,725,572 A | 3/1998 | Lam et al. | |
| 5,860,999 A | * 1/1999 | Schnepp-Pesch et al. | 606/191 |
| 6,117,167 A | 9/2000 | Goicoechea et al. | |
| 6,123,722 A | 9/2000 | Fogarty et al. | |
| 6,156,064 A | 12/2000 | Chouinard | |
| 6,159,239 A | 12/2000 | Greenhalgh | |
| 6,168,619 B1 | 1/2001 | Dinh et al. | |
| 6,183,508 B1 | 2/2001 | Stinson et al. | |
| 6,183,509 B1 | 2/2001 | Dibie | |
| 6,221,099 B1 | 4/2001 | Andersen et al. | |
| 6,221,100 B1 | 4/2001 | Strecker | |
| 6,221,102 B1 | 4/2001 | Baker et al. | |
| 6,224,625 B1 | 5/2001 | Jayaraman | |
| 6,228,111 B1 | 5/2001 | Tormala et al. | |
| 6,231,516 B1 | 5/2001 | Keilman et al. | |
| 6,240,616 B1 | 6/2001 | Yan | |
| 6,241,691 B1 | 6/2001 | Ferrera et al. | |
| 6,251,136 B1 | 6/2001 | Guruwaiya et al. | |
| 6,280,385 B1 | 8/2001 | Melzer et al. | |
| 6,325,822 B1 | * 12/2001 | Chouinard et al. | 623/1.15 |
| 6,350,279 B1 | * 2/2002 | McGuinness | 623/1.12 |

OTHER PUBLICATIONS

Adam, M.D., et al., *Interventional Magnetic Reconance Angiography*, Seminars In Interventional Radiology, vol. 16, No. 1, 1991, at 31–37.

Amano, M.D., et al., *Metallic Artifacts Of Cornoary and Iliac Arteries Stents In MR Angiography And Contrast–Enhanced CT*, Clinical Imaging, vol. 23, No. 2, 1999, at 239–240.

Amano, M.D., et al., *Metallic Artifacts Of Coronary And Iliac Arteries Stents In Mr. Angiography And Contrast–Enhanced CT*, Clinical Imaging, vol. 23, No. 2, Mar./Apr. 1999, at 85–89.

Bakker, et al., *MR–Guided Balloon Angioplasty: In Vitro Demonstration Of The Potential Of MRI For Guiding Monitoring, and Evaluating Endovascular Interventions*, JMRI, vol. 8, Jan./Feb. 1998, at 245–250.

CDRH Magnetic Resonance Working Group, *A Primer on Medical Device Interactions With Magnetic Resonance Imaging Systems*, http://www.fda/gov/cdrh/ode/primerf6.html, Mar. 5, 2000, at 1–18.

Primary Examiner—Corrine McDermott
Assistant Examiner—Hieu Phan
(74) Attorney, Agent, or Firm—Fulwider Patton Lee & Utecht, LLP

(57) ABSTRACT

An expandable metallic stent has discontinuities of non-conducting material. These eliminate electrically conducting paths in the stent rings and cells. This makes the stent easier to image with magnetic resonance imaging (MRI). The non-conducting material can include adhesives, polymers, ceramics, composites, nitrides, oxides, silicides, and carbides. The discontinuity is preferably shaped so that during expansion the discontinuity is placed in primarily a compressive stress.

41 Claims, 3 Drawing Sheets

OTHER PUBLICATIONS

Colombo, M.D., et al., *Biodegradable Stents "Fulfilling The Mission And Stepping Away"* Circulation 2000, Jul. 25, 2000, 202:371–373 http://www.circulationaha.org.

De Cobelli, et al., *MRI Assessment Of Coronary Stents Valutazione RM Delgi Stent Coronarici*, RAYS, vol. 24, No. 1, 1999 at 140–148.

Duerinckx, M.D., et al., *Assessment Of Coronary Artery Patency After Stent Placement Using Magnetic Resonance Angiography*, JMRI, vol. 8, No. 4, Jul./Aug. 1998, at 896–902.

Friedrich, et al., *Behavior Of Implantable Coronary stents During Magnetic Resonance Imaging*, Internaitonal Journal of Cardiovascular Interventions, vol. 2, at 217–222.

Girard, et al., *Wallstent Metallic Biliary Endoprosthesis: MR Imaging Characteristics*, Radioology, vol. 184, No. 3, at 874–876.

Hilfiker, M.D, et al., *Plain and Covered Stent–Grafts: In Vitro Evaluation Of Characteristics At Three–Dimensional MR Angiography*, Radiology, vol. 211, No. 3, Jun. 1999, at 693–697.

Hug, M.D. et al., *Cornary Arterial Stents: Safety and Arifacts During MRI Imagining*, Radiology 2000, vol. 216, Nov. 3, at 781–787.

Kee, M.D., et al, *MR–Guided Transjugular Portosystemic Shunk Placement In A Swine Model*, JVIR, vol. 10, No. 5, May 1999, at 529–535.

Laissy, et al., *Magnetic Resonance Angiography of Intravascular Endoprotheses: Investigation Of Three Devices*, Cardiovascular and Interventional Radiology, vol. 18, 1995, at 360–366.

Lardo, Ph.D., *Real–Time Magnetic Resonance Imagining: Diagnostic and Interventional Applications*, Pediatric Cardiology vol. 21, 2000, at 80–98.

Lenhart, M.D., et al., *Stent Appearance at Contrast–Enhanced MR Angiography: In Vitro Examination with 14 Stents*, Radiology Oct. 2000, vol. 271, No. 1, at 173–178.

Lufkin, et al., *Interventional MRI:Update*, European Radiology, vol. 7, (Suppl. 5), 1997 at 187–200.

Manke, C., *Stentagioplastie von Beckenarterienstenosen unter MRT–Kontrolle:Erste klinische Ergebnisse*, Fotschr Röntgenstr, 2000:172, at 92–97.

Makne, MD, et al, *Magnetic Resonance Monitoring of Stent Deployment In Vitro Evaluation of Different Stent Designs and Stent Delivery Systems*, Investigative Radiology, vol. 35, No. 6, Jun. 2000, at 343–351.

Matsumoto,. et al, *Gadolinium Enhanced MR Imagining Of Vascular Stents*, Journal of Computer Assisted Tomography, vol. 14, No. 3, May/Jun., 1990, at 357–361.

Matsumoto, et al., *Tantalum Vascular Stents: In Vivo Evaluation With MR Imagining*, Radiology, vol. 170, No. 3, Mar. 1989, at 753–755.

Nitatori, et al., *MRI Artifacts of Metallic Stents Derived From Imaging Sequencing And The Ferromagnetic Nature Of Materials*, Radiation Medicine, vol. 17, No. 4, 1999, at 329–334.

Omary, M.D. et al, *MR–Guided Angioplasty Of Renal Artery Stenosis In A Pig Model: A Feasibility Study*, J. JVIR 2000; vol. 11, at 373–381.

Schenck, *The Role Of Magnetic Susceptibiltiy In Magnetic Resonance Imaging: MRI Magnetic Compatibility Of The First and Second Kinds*, Medical Physics, vol. 23, No. 6, Jun. 1996, at 815–850.

Shellock,, *Metallic Stents: Evaluation of MR Imaging Safety*, AJR, vol. 173, Sep. 1999, at 543–547.

Strom, et al., *safety Of Implantable Coronary Stents During 1 H–Magnetic Resonance Imaging at 1.0 and 1.5 T*, Journal of Cardiovascular Magnetic Resonance vol.1, No. 3, 1999, at 239–245.

Stroman, et al., *Will It Be Feasible To Insert Endoprostheses Under Interventional MRI?*, J Endovasc–Surg, vol. 3, 1996, at 396–404.

Taal, et al., *Potential Risks And Atifacts Of Magnetic Resonance Imaging Of Self–Expandable Esophageal Stents*, Gastrointestinal Endoscopy, vol. 46, No. 5, 1997, at 424–429.

Tamai, M.D. et al., *Initial and 6–Month Results of Biodegradable Poly–l–Lactic Acid Coronary Stents In Humans*, Circulation, Jul. 25, 2000, at 399–404 http://www.circulationaha.org.

Tamai, M.D., et al., *A Biodegradable Poly–l–Lactic Acid Coronary Stent In The Porcine Coronary Artery*, Journal of Interventional Cardiology, vol. 12, No. 6, 1999 at 443–449.

Tsuji, MD, et al, *Experimental and Clinical Studies of Biodegradable Polymeric Stents*, Journal of Interventional Cardiology, vol. 13, Nov. 6, 2000, at 439–445.

Wendt, et al., *Visualisation, Tracking And Navigation Of Instruments For MRI–Guided Interventional Procedures*, Min Invas Ther & Allied Technol, vol. 8, No. 5, at 317–326.

* cited by examiner

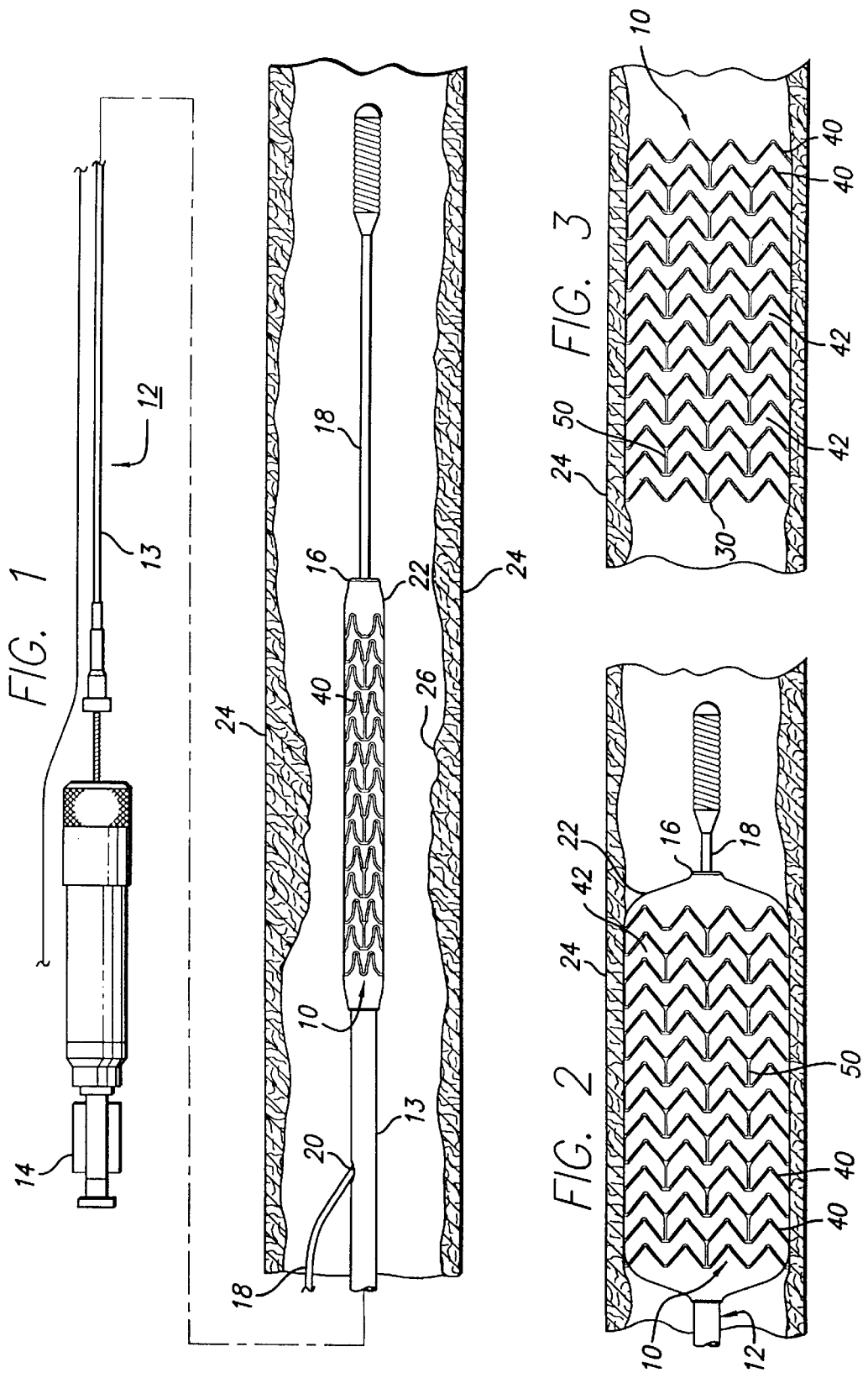

MRI COMPATIBLE STENT

FIELD OF THE INVENTION

This invention relates to stents, such as those placed in a human body to hold open a stenosed lumen. In particular, the invention relates to metal stents that can be viewed effectively by magnetic resonance imaging (MRI).

BACKGROUND OF THE INVENTION

Currently, x-ray fluoroscopy is the preferred imaging modality for cardiovascular intervention procedures, such as balloon angioplasty with stents. The visualization and tracking of stents under fluoroscopy is accomplished either by the stent's inherent adsorption of x-rays or by the placement of radiopaque markers. At this time, no other method has the temporal or spatial resolution of fluoroscopy. Nonetheless, fluoroscopy has drawbacks for both patient and clinician. Catheterization is required in order to directly inject a high concentration of iodinated contrast agent into the coronary arteries. Systemic administration of the contrast agent is not practical, as it would require too high a dose. Furthermore, iodinated contrast agents are nephrotoxic, with a low but measurable incidence of short-term renal failure. Allergic reactivity also serves a contraindication for certain patients. Fluoroscopy also uses ionizing x-ray radiation, with its attendant hazards. This is an issue for the patient during protracted or repeat interventions. It is a also a daily issue for medical personnel, who must cope with the burden of their own dose monitoring and of wearing lead shielding.

Fluoroscopy generates a two-dimensional projection image of what are three-dimensional structures. This requires multiple views to appraise complex vasculature. Another imaging modality, which has the potential to supplant fluoroscopy and become important in the diagnostic imaging of stents, is magnetic resonance imaging (MRI). One advantage of MRI is that it is a tomographic imaging technique that generates a 3-D data set of the imaged tissue. Consequently, the data set can be manipulated to show different imaging planes and slice thicknesses. This permits high quality transverse, coronal and sagittal images to be obtained directly. MRI has greater soft tissue contrast and tissue discrimination than computed tomography (CT) or other x-ray based imaging modalities, such as angiography. As another advantage, MRI also does not use ionizing radiation and does not require catheterization to image the vasculature.

The technique of MRI encompasses the detection of certain atomic nuclei (those possessing magnetic dipole moments) utilizing magnetic fields and radio-frequency (RF) radiation. It is similar in some respects to x-ray computed tomography in providing a cross-sectional display of the body organ anatomy, only with excellent resolution of soft tissue detail. In its current use, the images constitute a distribution map of protons, and their properties, in organs and tissues. However, unlike x-ray computer tomography, MRI does not use ionizing radiation. The fundamental lack of any known hazard associated with the level of the magnetic and radio-frequency fields that are employed renders it possible to make repeated scans. Additionally, any scan plane can readily be selected, including transverse, coronal, and sagittal sections. MRI is, therefore, a safe non-invasive technique for medical imaging.

The hydrogen atom, having a nucleus consisting of a single unpaired proton, has one of the strongest magnetic dipole moments of nuclei found in biological tissues. Since hydrogen occurs in both water and lipids, it is abundant in the human body. Therefore, MRI is most commonly used to produce images based upon the distribution density of protons and/or the relaxation times of protons in organs and tissues. The majority of the signal in MRI comes from water. Tissues vary in their water content, but for angiography, blood is the relevant tissue. Blood is approximately 93% water. This translates into a proton concentration of 103 moles/liter. However, MRI can image tissues with a lower water content. For example, grey matter and bone are 71% and 12% water respectively. It must be noted that MRI can image proton concentrations much lower than those of blood or grey matter. Image resolution is determined by the signal to noise (S/N) ratio. Faster acquisition of data or longer acquisition times both increase the signal to noise ratio.

MRI is presently used for diagnostic applications, but interventional MRI is an active area of research. For devices to be seen under MRI, they must be MRI "compatible." In the context of a diagnostic or interventional procedure, this refers to the ability to accurately image a stent. MRI imaging schemes for devices are divided into two categories, active and passive. Active imaging requires some sort of electrical circuit on, or electrical connection to, the device. This presently is not an easily implemented solution for small, free-standing devices such as stents. The passive imaging scheme that applies readily to metal stents is based on the stent material's magnetic susceptibility and electrical conductivity.

Because stents are constructed of electrically conductive materials, they suffer from a Faraday Cage effect when used with MRI's. Generically, a Faraday Cage is a box, cage, or array of electrically conductive material intended to shield its contents from electromagnetic radiation. The effectiveness of a Faraday Cage depends on the wave length of the radiation, the size of the mesh in the cage, the conductivity of the cage material, its thickness, and other variables. Stents do act as Faraday Cages in that they screen the stent lumen from the incident RF pulses of the MRI scanner. This prevents the proton spins of water molecules in the stent lumen from being flipped or excited. Consequently, the desired signal from the stent lumen is reduced by this diminution in excitation. Furthermore, the stent Faraday Cage likely impedes the escape of whatever signal is generated in the lumen. The stent's high magnetic susceptibility, however, perturbs the magnetic field in the vicinity of the implant. This alters the resonance condition of protons in the vicinity, thus leading to intravoxel dephasing with an attendant loss of signal. The net result with current metallic stents, most of which are stainless steel, is a signal void in the MRI images. Other metallic stents, such as those made from Nitinol, also have considerable signal loss in the stent lumen due to a combination of Faraday Cage and magnetic susceptibility effects.

At this time, MRI is being used to non-invasively image many regions of the vasculature. The comprehensive cardiac MRI exam has demonstrated clinical utility in the areas of overall cardiac function, myocardial wall motion, and myocardial perfusion. It may become the standard diagnostic tool for heart disease. With these advances in imaging technologies, a stent that can be meaningfully imaged by MRI in an optimal manner would be advantageous. A non-metallic stent obviously solves the imaging problem. Metals, however, are the preferred material as they make strong, low profile stents possible. Unfortunately, most metal stents, particularly of stainless steel, obliterate MRI images of the anatomy in their vicinity and obscure the stent lumen in the image. By reducing the amount of metal in the stent, or by making the cells larger, or by having fewer cells, the Faraday Cage effect may be reduced. The RF radiation used in MRI has a wavelength of 2 to 35 meters depending on the scanner and environment of the stent. Therefore, the cell sizes of stents are already much smaller than the RF wavelength. Increasing the stent cell size would work only primarily by decreasing the amount of metal. This solution is limited by the need for stents to have adequate radial strength and scaffolding.

Stents commonly have some form of ring elements. These are the portions of the stent that both expand and provide the radial strength. These ring elements are joined by links of various sorts. This combination of rings and links creates enclosed cells, and taken together, they create many continuous loops of metal. These loops can run around the circumference of the stent, or they can run in portions of the sent wall. Examination of any modern stent pattern will show a variety of hoops, rings, loops, or cells that provide many electrically conductive paths. It is this structure that creates a Faraday Cage, and its associated problems with MRI. Examples of such structures can be found in the *Handbook of Coronary Stents*, edited by Serruys and Kutryk. Another such stent is disclosed in U.S. patent application Ser. No. 09/753,232 to Hong and Limon, filed Dec. 28, 2000, and assigned to Advanced Cardiovascular Systems, Inc. (ACS), the assignee of the present application. In that application, the inventors disclose a hybrid stent with metal rings and polymer connecting links. The polymer links prevent current flow between rings, but the rings themselves represent complete potential current paths that still impede meaningful imaging through MRI.

In the United States, the most popular stent configurations appear in the: 1) MultiLink® family developed by ACS, which is now selling later developed models like the Tetra®; 2) the NIR® stent, sold in the United States by Boston Scientific Corp. and SciMed Life Systems, Inc.; 3) the MicroStent® family developed by Medtronic AVE, including the latest generation of stents, the "S" series; and, 4) the BX Velocityg by Cordis Corp., successor to a variety of stents including the PalmazSchatz, Crown, and MiniCrown models. A challenge is how to break up a stent pattern's many conductive paths that form a Faraday Cage, thus permitting a clear MRI image of the stent lumen while still maintaining the strength and mechanical function of the stent. Stents which can be imaged, non-invasively, by MRI for both their lumen and surrounding tissues will have greater clinical utility than those which cannot. Such clinical utility often translate into commercial success. This is particularly true if the device allows a non-invasive procedure versus an invasive one. Once patients become aware of a non-invasive alternative, they tend to demand it.

SUMMARY OF THE INVENTION

To eliminate or reduce the Faraday Cage effect, one approach is to break up the continuous, metallic, electrically conductive paths in the stent pattern.

The present invention is a generally cylindrical metal tube. The tube has apertures, so that the stent comprises electrically conductive cells and circumferential rings. The metal tube also comprises a plurality of electrical discontinuities that include an electrically non-conducting material. The electrically non-conducting material can be a polymer or an adhesive. It can also be a ceramic or a composite material.

In one embodiment, the electrical discontinuities are in circumferential rings. In another embodiment, the electrical discontinuities can be in cells that are formed in the metal tube. In yet another embodiment, the discontinuities are in both the rings and cells.

The stent is formed from a tube by laser cutting the pattern of cylindrical rings in the tube. The stent also may be formed by laser cutting a flat metal sheet in the pattern of the cylindrical rings and links, and then rolling the pattern into the shape of the tubular stent and providing a longitudinal weld to form the stent. In either case, the preferred method would be to then cut the stents to form the discontinuities. Another alternative is to weld rings together. Electrical discontinuities can be placed in the rings before or after welding.

BRIEF DESCRIPTION OF THE DRAWINGS

FIG. 1 is an elevation view, partially in section, of a stent which is mounted on a rapid-exchange delivery catheter and positioned within an artery.

FIG. 2 is an elevation view, partially in section, similar to that shown in FIG. 1, wherein the stent is expanded within the artery so that the stent embeds within the arterial wall.

FIG. 3 is an elevation view, partially in section, showing the expanded stent implanted within the artery after withdrawal of the rapid-exchange delivery catheter.

DETAILED DESCRIPTION OF THE PREFERRED EMBODIMENTS

Figure 4:
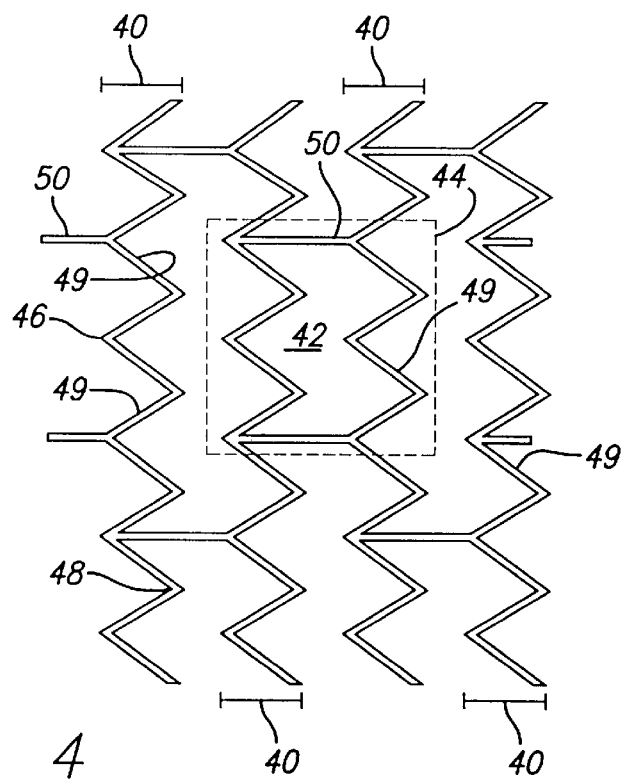
FIG. 4 represents part of a stent, flattened to more clearly depict features of the present invention.

The present invention improves existing endovascular prostheses, such as metal stents, by making them more compatible with MRI imaging. The MRIinduced oscillating magnetic fields are prevented from inducing electrical current in the continuous electrical paths of the stent by the use of non-conducting materials. These materials are placed in breaks, or electrical discontinuities, in the stent where they act as electrical insulators.

FIGS. 1–3 depict a typical equipment configuration for a balloon expandable stent. FIGS. 4–8 depict specific details of the present invention.

FIG. 1 of the drawings depicts a stent 10 mounted on a catheter assembly 12 which is used to deliver a stent and implant it in a body lumen, such as a coronary artery, peripheral artery, or other vessel or lumen within the body. The catheter assembly includes a catheter shaft 13 which has a proximal end 14 and a distal end 16. The catheter assembly is configured to advance through the patient's vascular system by advancing over a guide wire by any of the well known methods of an over-the-wire system (not shown) or a well known rapid exchange (RX) catheter system, such as the one shown in FIG. 1.

Catheter assembly 12 depicted in FIG. 1 includes an RX port 20 where the guide wire 18 exits the catheter. The distal end of the guide wire 18 exits the catheter distal end 16, so that the catheter advances along the guide wire on a section of the catheter between the RX port 20 and the catheter distal end 16. As is known in the art, the guide wire lumen which receives the guide wire is sized for receiving various diameter guide wires to suit a particular application. The stent 10 is mounted on an expandable member 22 such as a balloon and is crimped tightly thereon, so that the stent and expandable member present a low profile diameter for delivery through the arteries.

As shown in FIG. 1, a partial cross-section of an artery 24 has a small amount of plaque that has been previously treated by an angioplasty or other repair procedure. In a procedure presently known in the art as direct stenting, stents can also be placed without prior angioplasty or other procedures. Stent 10 is used to repair a diseased or damaged arterial wall as shown in FIG. 1, or a dissection, or a flap, all of which are commonly found in the coronary arteries and other blood vessels.

In a typical procedure to implant stent 10, the guide wire 18 is advanced through the patient's vascular system by well known methods so that the distal end of the guide wire is advanced past the plaque or diseased area 26. Prior to implanting the stent, the cardiologist may wish to perform an angioplasty or other procedure (i.e., atherectomy) in order to open and remodel the vessel and the diseased area. Thereafter, the stent delivery catheter assembly 12 is advanced over the guide wire so that the stent is positioned in the target area. The expandable member or balloon 22 is inflated by well known means so that it expands radially outwardly and in turn expands the stent radially outwardly until the stent is apposed to the vessel wall. The expandable member is then deflated and the catheter withdrawn from the patient's vascular system. The guide wire typically is left in the lumen for post-dilatation procedures, if any, and subsequently is withdrawn from the patient's vascular system. As depicted in FIG. 2, the balloon is fully inflated with the stent expanded and pressed against the vessel wall. In FIG. 3, the implanted stent remains in the vessel after the balloon has been deflated and the catheter assembly and guide wire have been withdrawn from the patient.

Stent 10 holds open the artery after the catheter is withdrawn, as illustrated by FIG. 3. Due to the preferred formation of the stent from an elongated tubular member, the straight and undulating components of such a stent are relatively flat in transverse cross-section, so that when the stent is expanded, it is pressed into the wall of the artery and as a result does not interfere with the blood flow through the artery. The stent is pressed into the wall of the artery and will eventually be covered with endothelial cell growth which further minimizes blood flow interference. The undulating portion of the stent provides good tacking characteristics to prevent stent movement within the artery. Furthermore, the cylindrical rings closely spaced at regular intervals, provide uniform support for the wall of the artery, and consequently are well adapted to tack up and hold in place small flaps or dissections in the wall of the artery, as illustrated in FIGS. 2 and 3.

The stent 10 depicted in FIGS. 1–3 is merely representative of a typical metal stent. The present invention contemplates that the stent could be a NIR® stent sold by Boston Scientific Corporation and SciMed Life Systems, Inc., the "S" series stent manufactured by Medtronic AVE, Inc., or a Tetra® stent manufactured by Advanced Cardiovascular Systems, Inc. (ACS). The present invention covers virtually any metallic stent, such as those described in the latest edition of the *Handbook of Coronary Stents*, edited by Serruys and Kutryk. Other, future patterns of metal stents will likely be usable with the present invention. So, too, are those stents used in the United States during the last ten years, including those expressly identified in the background section above. The preceding discussion has focused on balloon expandable stents, although the present invention can be used with self-expanding stents.

All of these stents have general, common characteristics. Whether they are formed from stainless steel, nickel titanium alloy, or other metals, they are all electrically conductive. These stents are also formed in a hollow, generally cylindrical shape with apertures in the shell of the tube, thus forming a Faraday Cage. The stent 10 in FIGS. 1–3 is such a stent, conceptually representing a stent similar to that of the ACS Tetra®. The stent 10 comprises of plurality of cylindrical rings 40, which extend circumferentially around the stent 10. The cylindrical rings 40 are connected by links or connectors 50. Together, the rings 40 and connectors 50 make these stents into a hollow, tube-like structure with apertures 42. Typically, since the stent in its preferred embodiment is laser cut from a solid cylindrical tube, there are not discrete parts, such as rings 40 and connectors 50, that are assembled into the stent 10. The stent is preferably a monolithic structure. Other manufacturers have, however, formed stents out of flat sheets with openings, with the sheets being rolled into tubes and welded. Others have actually formed individual rings and welded or connected them together. The present invention contemplates all of these forms of manufacturing and physical configurations.

When an oscillating magnetic field is applied in the vicinity of a stent, such as stent 10 in FIG. 3, electrical currents are induced in stent 10. Depending upon the nature of the magnetic field, an MRI could induce currents in some or all of rings 40 and cells 44 depicted in FIG. 4. Currents induced around the entire perimeter or circumference of stent 10, such as through rings 40, are expected to be the most problematic for MRI, although currents in cells 44 also cause signal distortion or attenuation.

FIG. 4 is a partial, simplified version of a stent pattern that can be used in the present invention. FIG. 4 depicts four cylindrical rings 40. While the figure itself depicts the ring as flat and linear, one who is skilled in the art will appreciate that in three dimensions the ring is a continuous structure. Each ring 40 has a shape that has been called, at various times, undulating, corrugated, or sinusoidal. Each ring has a series of peaks 46 and valleys 48. The peaks and valleys are formed by segments 49 that have been called struts, bar arms and other terms. Each ring is connected by at least one connector 50. The number and configuration of connectors 50 is not a significant aspect of the invention, and is a matter of choice for one of skill in the art, as is the configuration of the ring 40. Connectors can even simply be welds between two rings. Whether the ring is cylindrical or whether its configuration is more irregular than that depicted in FIG. 4 is again a matter of choice for those of skill in the art. Using FIG. 4 as an example, stents can also be considered to have a cellular structure. Cell 44 is defined by two portions of rings 40 and two connectors 50, with aperature 42 in the center of the cell. Thus, in the context of MRI, metallic stents represent a series of complete, electrically conductive circuits defined by rings 40, cells 44, or both, depending upon the pattern of the apertures 42 in the stent.

Figure 5:
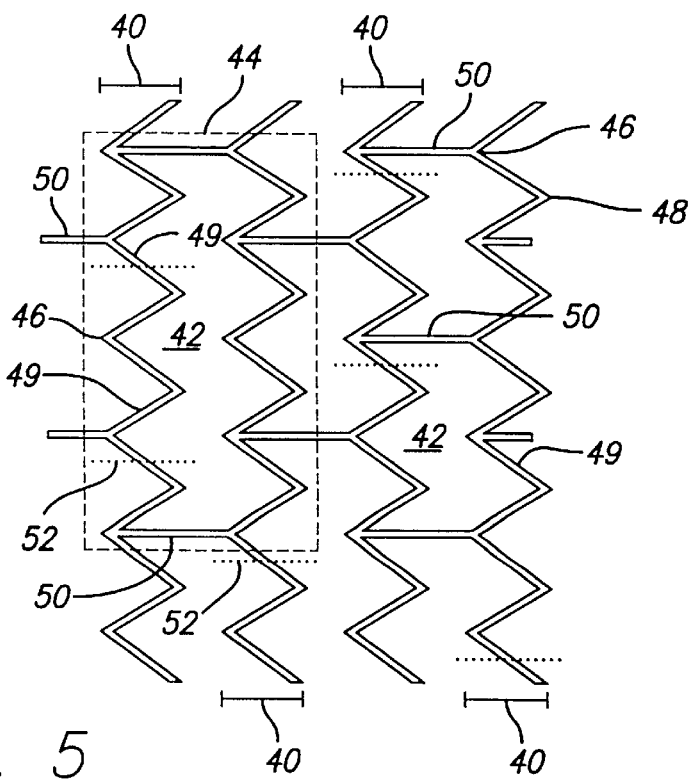
FIG. 5 is a view like that FIG. 4, with the additional lines indicating breaks in the conducting pattern of the stent.

FIG. 5 is similar to FIG. 4 except that it additionally depicts discontinuities 52 in cylindrical rings 40. The purpose of the discontinuities is to eliminate a complete electrically conducting circuit through which an electrical current could travel if the current were induced in the stent by an MRI procedure. The location of discontinuities 52 is also a matter of choice. In the preferred embodiment, however, the discontinuities 52 are located to eliminate any complete electrically conducting circuits in both the rings 40 and the cells 44. Although not depicted in FIG. 5, discontinuities 52 could also be placed in the connectors 50.

Figure 6:
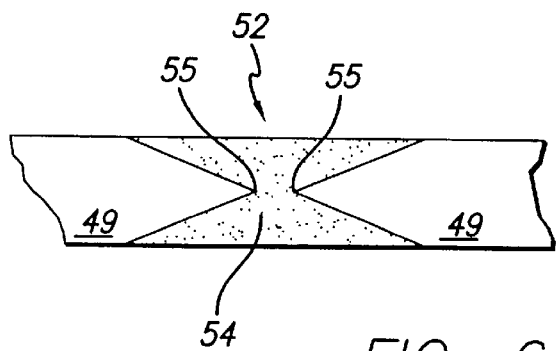
FIG. 6 depicts one type of joint that breaks the electrical conductivity.

FIG. 6 depicts one possible embodiment of the discontinuities 52 of the present invention. In a preferred method, a continuous strut 49 has been cut by a laser to form discontinuity 52. If such cuts were made without reattaching the cut portions of struts 49, the stent 10 would break into a number of pieces. Therefore, the cut portions of strut 49 must be structurally reconnected so that the stent will function for its intended purpose of supporting a lumen. That reattachment should be made with an electrically nonconducting material, such as an adhesive or polymer 54. Adhesives and polymers are the preferred choices, because they can be selectively applied with a tiny needle. A polymeric material used as part of the electrical discontinuity will not itself perturb the MRI image, or even be that visible. The reason is that even though the majority of polymers contain hydrogen nuclei, the resonance signals from protons in polymers are broad and chemically shifted from the water proton signal from which the majority of the MRI signal is derived. Polymeric catheters, for example, show up as regions of little or no signal under MRI (signal voids). In the present invention, it is anticipated that polymers, and other electrically non-conductive materials, will enhance accurate stent imaging by diminishing the Faraday Cage effect while themselves not contributing to the MRI image.

The materials used in electrical or electromagnetic devices can be classified in three categories: 1) insulators, 2) conductors, and 3) semiconductors. The material 54 used in electrical discontinuity 52 should have insulating characteristics. It is possible that the material 54 could include semiconductors as well as insulators, if the resistivity of material 54 is high enough at the induced voltage to avoid current flow through the semiconductor. As such, the materials 54 used in discontinuity 52 should not be limited, and, for the present invention, semiconductors may be thought of as insulators. Besides polymers and adhesives, such materials could include ceramics and composites. The materials used in the discontinuity could also include compounds using elements from the trivalent, quadravalent, and pentavalent columns of the periodic table, such as nitrides, oxides, silicides, and carbides.

As improvements in MRI hardware and software continue, in the future it may not be necessary to create complete discontinuities in the stent structure. For example, if the points 55 of the cut portions of struts 49 in FIG. 6 were just touching, it is likely that the size of the current passing through strut 49 would be substantially smaller than if strut 49 had its full, continuous cross section. The struts 49 and links 50 in FIG. 4 would have a greater conducting cross sectional area than if the points 55 of struts 49 in FIG. 5 were just touching. Therefore, they would carry substantially more current. It may be that further advancements in MRI and signal processing technology will allow for the presence of such electrical current. To the extent that such future developments would, in fact, occur, the present invention contemplates that the term discontinuity should be considered relative to the effectiveness of the MRI technology and may in fact not be completely discontinuous, but merely narrower and substantially less conductive than adjacent, conductive portions of the stent. The discontinuity must also include an insulating material.

Figure 7:
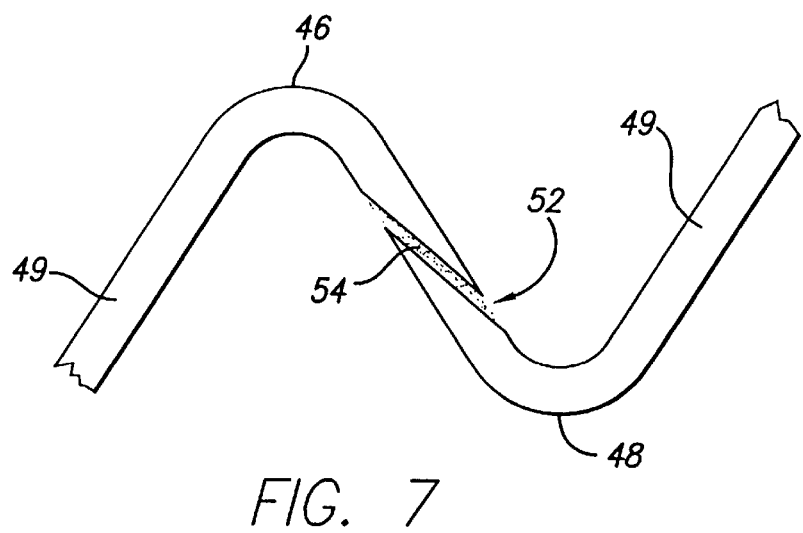
FIG. 7 depicts another type of joint that breaks the electrical conductivity.

Nearly all electrically insulating materials are weaker than metals. Therefore, a preferred embodiment of the present invention would place the material 54 in discontinuity 52 under compression. Most materials are stronger under compression than under shear, tension, or bending. Assuming the forces from the expansion of the balloon 22 are the greatest forces on a stent, the joint depicted in FIG. 7 would place the material 54 in discontinuity 52 under compression during a stent's expansion. The thickness of the discontinuity 52 in FIG. 7 is exaggerated for the sake of clarity.

Figure 8:
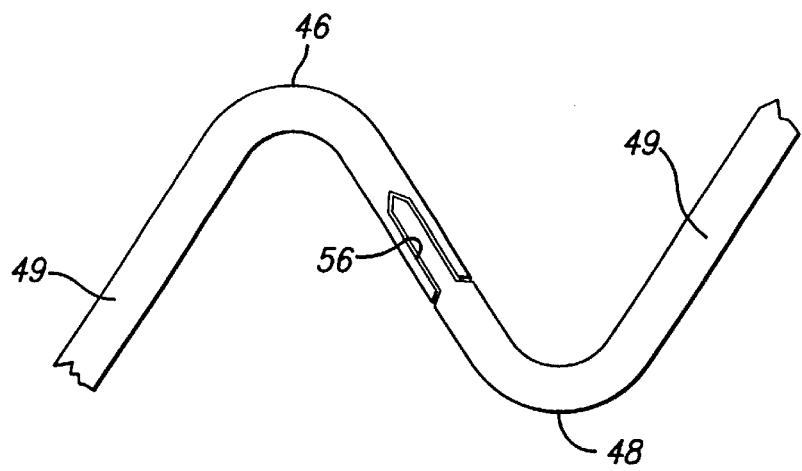
FIG. 8 depicts yet another type of joint that breaks the electrical conductivity.

Other joint configurations are also possible. FIG. 8 depicts a tongue-in-groove shape. This configuration would resist shear forces in either direction of strut 49, as long as those forces are in a plane defined by the outer surface of the stent. Therefore, the preferable method of manufacturing the present invention would be to use a hollow cylindrical tube with a flat surface, and to cut the stent with precision laser technology. Nevertheless, as noted above, the present invention contemplates other methods of manufacture. Such methods could include creating a piece of flat metal with the stent pattern cut or etched out, and then rolling the flat piece into a tube. Another method would include welding rings together, without or without a separate metallic link between the rings. The timing of cutting and forming the discontinuities would be a matter of choice to one of skill in the art.

While the invention has been illustrated and described above, those skilled in the art will appreciate that the stent can be constructed and configured in a variety of ways. Particular sizes and dimensions, the number of crowns per ring, the type of materials used, and the like have been described and are provided as examples only. Other modifications and improvements may be made without departing from the scope of the invention, such as using other shapes and insulators for the electrical discontinuities. For example, one could make the discontinuities as dovetail shapes. In the broadest sense, the invention covers any endovascular prosthesis, including stents and grafts, made primarily of metal. In balloon expandable form, such prostheses can be used for coronary, neurological, saphenous vein graft, renal, protected iliac, biliary, or other protected regions of the circulatory system. In self-expanding form, the invention may be used in unprotected regions of the vasculature such as the carotid or femoral arteries. In fact, the invention can be used as a prosthesis with any method of expansion, or even as a graft that does not require expansion. The invention may be of meandered wire or coil, as well as the designs discussed above. Covered stents consisting of a metal frame with a woven fabric or polymeric covering could incorporate this concept. Coatings may be placed on the invention to improve hemocompatibility, biocompatibility, or for drug delivery.

What is claimed:

1. An expandable metallic stent, for use in a body lumen, that can be visualized by magnetic resonance imaging, comprising:
   a generally cylindrical metal tube with apertures that form a cage of electrically conducting cells and circumferential rings in the stent that shield the body lumen from electromagnetic radiation generated by magnetic resonance imaging; and
   a plurality of electrical discontinuities in the metal tube to substantially reduce or eliminate the shielding of the body lumen from electromagnetic radiation, the discontinuities including an electrically non-conducting material.

2. The stent of claim 1, wherein the electrical discontinuities are configured so as to be subject to primarily a compressive force during the expansion of the stent.

3. The stent of claim 2, wherein the electrical discontinuities comprise a diagonal shape.

4. The stent of claim 2, wherein the electrical discontinuities comprise a tongue-in-groove shape.

5. The stent of claim 2, wherein the electrical discontinuities are only in the circumferential rings.

6. The stent of claim 5, wherein all of the circumferential rings have electrical discontinuities.

7. The stent of claim 5, wherein the electrical discontinuities comprise an adhesive.

8. The stent of claim 2, wherein the electrical discontinuities are only in the cells.

9. The stent of claim 8, further comprising electrical discontinuities in the circumferential rings.

10. The stent of claim 9, wherein the stent is balloon expandable.

11. The stent of claim 9, wherein the stent is self-expanding.

12. The stent of claim 8, wherein the electrical discontinuities comprise a polymer.

13. The stent of claim 1, wherein the electrical discontinuities are in the rings and in the cells.

14. The stent of claim 13, wherein the non-conducting material is one of a composite and a ceramic.

15. The stent of claim 13, wherein the non-conducting material is at least one of an adhesive and a polymer.

16. An expandable metallic stent for use in a body lumen and with an improved visibility for MRI, comprising:

a plurality of metallic, electrically conducting rings and cells that form a cage that shields the body lumen from electromagnetic radiation, each ring defining a generally cylindrical surface;

at least one connector connecting each ring to an adjacent ring, the connectors and the adjacent rings forming at least one cell;

an electrical discontinuity in a plurality of the rings to substantially reduce or eliminate the shielding of the body lumen from electromagnetic radiation, the discontinuity being configured so as to be subject to primarily a compressive force during the expansion of the stent; and an electrically non-conducting material disposed in each discontinuity.

17. The stent of claim 16, wherein a plurality of connectors include an electrically non-conducting material.

18. The stent of claim 16, wherein the non-conducting material is one of a composite and a ceramic.

19. The stent of claim 16, wherein the non-conducting material is at least one of an adhesive and a polymer.

20. The stent of claim 16, further comprising an electrical discontinuity in at least one cell.

21. In a metallic, expandable stent for use in a body lumen and comprised of interconnected, electrically conducting rings, the stent having an improved visibility to electromagnetic radiation of MRI, the improvement comprising:

an electrical discontinuity, disposed in a plurality of the rings, to substantially reduce or eliminate shielding of the body lumen from electromagnetic radiation caused by MRI.

22. The improvement to the stent of claim 21, wherein the electrical discontinuity includes an electrically non-conducting material that is one of a polymer, an adhesive, a ceramic, a composite material, a nitride, a silicide, a carbide, and an oxide.

23. The improvement to the stent of claim 22, wherein the electrically non-conducting material is disposed so as to be subject to primarily a compressive force during expansion of the stent.

24. In a metallic, expandable stent for use in a body lumen and comprised of a plurality of electrically conducting cells with an improved visibility to electromagnetic radiation of MRI, the improvement comprising:

an electrical discontinuity, disposed in a plurality of cells and including an electrically non-conducting material, to substantially reduce or eliminate the shielding of the body lumen from the electromagnetic radiation caused by the MRI.

25. The improvement to the stent of claim 24, wherein the electrically non-conducting material is disposed so as to be subject to a primarily compressive force during expansion of the stent.

26. The improvement to the stent of claim 25, wherein the non-conducting material is a composite.

27. The improvement to the stent of claim 25, wherein the non-conducting substance is at least one of a ceramic, polymer, nitride, carbide, silicide and oxide.

28. The improvement to the stent of claim 25, wherein the non-conducting substance is an adhesive.

29. The improvement to the stent of claim 25, wherein the discontinuity is a diagonal shape.

30. The improvement to the stent of claim 25, wherein the discontinuity is a tongue-in-groove shape.

31. The improvement to the stent of claim 25, wherein the discontinuity is a dovetail shape.

32. In a metallic endoluminal prosthesis having a cage of electrical current paths inducible by MRI, the improvement comprising:

a plurality of electrical discontinuities having an electrically non-conducting material, the discontinuities being disposed in the current paths to substantially reduce or eliminate MRI induced current in the cage.

33. The improvement to the stent of claim 32, wherein the electrically non-conducting material is subject to a primarily compressive force during placement or use of the prosthesis.

34. The improvement to the stent of claim 32, wherein the non-conducting material is a composite.

35. The improvement to the stent of claim 32, wherein the non-conducting material is at least one of a ceramic, polymer, nitride, carbide, silicide and oxide.

36. The improvement to the stent of claim 32, wherein the non-conducting material is an adhesive.

37. The improvement to the stent of claim 32, wherein the discontinuities are a diagonal shape.

38. The improvement to the stent of claim 32, wherein the discontinuities are a tongue-in-groove shape.

39. The improvement to the stent of claim 32, wherein the discontinuities are a dovetail shape.

40. An expandable metallic stent for use in a body lumen and with an improved visibility for MRI, comprising:

a plurality of metallic, electrically conducting rings and cells that form a cage shielding the body lumen from electromagnetic radiation from the MRI, each ring defining a generally cylindrical surface;

at least one connector connecting each ring to an adjacent ring, the connectors and adjacent rings forming at least one cell;

an electrical discontinuity in a plurality of the cells to substantially reduce or eliminate the shielding of the body lumen from electromagnetic radiation from the MRI, the discontinuity being configured so as to be subject to primarily a compressive force during the expansion of the stent; and an electrically non-conducting material disposed in each discontinuity.

41. The stent of claim 40, wherein a plurality of the rings includes an electrical discontinuity having an electrically non-conducting material.

* * * * *